United States Patent [19]

Jordine

[11] Patent Number: 5,672,754

[45] Date of Patent: Sep. 30, 1997

[54] PROCESS FOR THE PREPARATION OF AMINODIPHENYLAMINE COMPOUNDS

[75] Inventor: Guido Jordine, Freiburg, Germany

[73] Assignee: Ciba-Geigy Corporation, Tarrytown, N.Y.

[21] Appl. No.: 528,586

[22] Filed: Sep. 15, 1995

[30] Foreign Application Priority Data

Sep. 16, 1994 [CH] Switzerland .............. 2839/94

[51] Int. Cl.$^6$ .................................. C07C 209/50
[52] U.S. Cl. .............................. 564/414; 564/406
[58] Field of Search ................. 564/406, 394, 564/414

[56] References Cited

U.S. PATENT DOCUMENTS 3,994,873  11/1976  Sommer et al. .................. 260/206
4,254,054  3/1981   Arndt et al. ..................... 260/510

FOREIGN PATENT DOCUMENTS 0010244  4/1980  European Pat. Off. .
0406629  1/1991  European Pat. Off. .
0257068  6/1988  German Dem. Rep. .
1521218  8/1978  United Kingdom .

OTHER PUBLICATIONS

Ber. dt. Chem., vol. 41, pp. 3744–3755, 1908.

J. Prakt. Chem., vol. 46, pp. 565–574, 1892.

Chemical Abstract, 115, 10847p (Apr. 1991).

CA62:16187(g). Jun. 1965.

CA51:2598(d). Jan. 1957.

CA58:2020(b) Feb. 1963.

CA54:6302(b) Apr. 1960.

*Primary Examiner*—Brian M. Burn
*Attorney, Agent, or Firm*—Kevin T. Mansfield; David R. Crichton

[57] ABSTRACT

The invention relates to a process for the preparation of compounds of formula

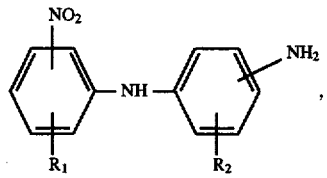

(1)

wherein $R_1$ is hydrogen, $C_1$–$C_4$ alkyl or sulfo, and $R_2$ is hydrogen or $C_1$–$C_4$ alkyl, which process comprises reacting a compound of formula

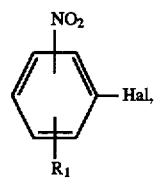

(2)

wherein Hal is halogen and $R_1$ has the meaning given above, with a compound of formula

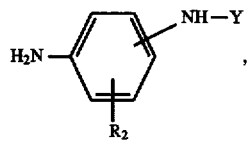

(3)

wherein Y is a saponifiable group and $R_2$ has the meaning given above, to give the compound of formula

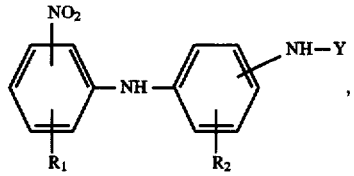

(4)

wherein $R_1$, $R_2$ and Y have the meanings given above, and saponifying the compound of formula (4) to give the compound of formula (1).

The compounds of formula (1) are suitable for the synthesis of dyes.

12 Claims, No Drawings

PROCESS FOR THE PREPARATION OF AMINODIPHENYLAMINE COMPOUNDS

The present invention relates to a process for the preparation of aminodiphenylamine compounds. These compounds are particularly suitable as intermediates for dyes.

In recent years, increasing efforts have been made to optimise the processes for the preparation of dyes and the intermediates thereof. In order to achieve satisfying results, it is necessary to rely on processes which enable the products to be obtained in highest possible yields, with a low number of by-products and in reproducibly good quality.

It has been found that this object is essentially achieved by the process described hereinafter.

Accordingly, the invention relates to a process for the preparation of compounds of formula

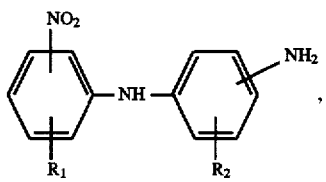

wherein $R_1$ is hydrogen, $C_1$–$C_4$alkyl or sulfo, and $R_2$ is hydrogen or $C_1$–$C_4$alkyl, which process comprises reacting a compound of formula

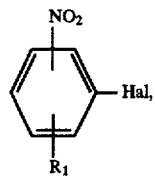

wherein Hal is halogen and $R_1$ has the meaning given above, with a compound of formula

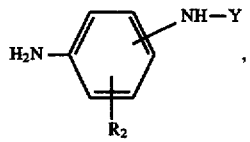

wherein Y is a saponifiable group and $R_2$ has the meaning given above, to give the compound of formula

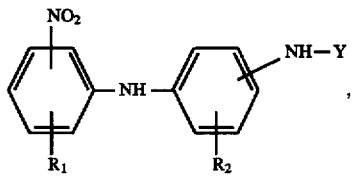

wherein $R_1$, $R_2$ and Y have the meanings given above, and saponifying the compound of formula (4) to give the compound of formula (1).

$R_1$ and $R_2$ defined as $C_1$–$C_4$alkyl are suitably each independently of the other e.g. methyl, ethyl, propyl, isopropyl, butyl, isobutyl, sec-butyl or tert-butyl, preferably methyl.

Hal defined as halogen is suitably e.g. chloro or bromo, preferably chloro.

Y defined as a saponifiable group may typically be $C_2$–$C_4$alkanoyl, such as acetyl or propionyl, or sulfomethyl. Y is preferably acetyl.

$R_1$ is preferably sulfo.

The preferred meaning of $R_2$ is hydrogen.

It is particularly preferred to use those compounds of formula (2), wherein the nitro group is para- or ortho-positioned relative to the substituent Hal.

It is very particularly preferred to use as compounds of formula (2) those of formula

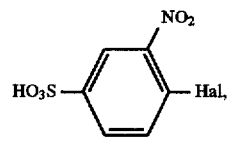

wherein Hal is halogen, preferably chloro.

Furthermore, it is very particularly preferred to use as compounds of formula (3) those of formula

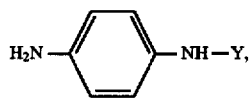

wherein Y has the meanings and preferred meanings given above.

It is preferred to use a compound of formula (5) together with a compound of formula (6).

The reaction of the compound of formula (2) with the compound of formula (3) is typically carried out in aqueous medium under normal or elevated pressure, conveniently at 1.1 to 6 bar, more particularly 1.1 to 4 bar and, preferably, 1.5 to 3 bar. It has been found that for this reaction the temperature is conveniently in the range from 80° to 150° C., preferably from 110° to 130° C. The reaction is preferably carried out in the presence of an alkali metal hydroxide, an alkali metal carbonate or an alkaline earth metal oxide, preferably in the presence of magnesium oxide. If alkali metal hydroxides or alkali metal carbonates are used, they are preferably added during the reaction.

Illustrative examples of alkali metal hydroxides, alkali metal carbonates and alkaline earth metal oxides are sodium hydroxide, sodium carbonate, magnesium oxide and calcium oxide. Among these, alkaline earth metal oxides are preferred, more particularly magnesium oxide or calcium oxide and, preferably, magnesium oxide.

In a preferred embodiment of the invention, the reaction of the compound of formula (2) with the compound of formula (3) is carried out in an inert gas atmosphere, preferably under nitrogen.

The saponification of the compound of formula (4) is typically carried out in aqueous medium and under normal or elevated pressure, typically at 1.1 to 6 bar, more particularly 1.1 to 4 bar and, preferably, 1.5 to 3 bar. It has been found that for this reaction the temperature is conveniently in the range from 80° to 120° C., preferably from 80° to 105° C. The saponification can be carried out in alkaline as well as in acid medium. It is preferred to carry out the saponification in acid medium, suitable acids for adjusting the pH being hydrochloric acid or sulfuric acid.

A particularly preferred embodiment of this invention comprises reacting a compound of formula (5), wherein Hal is halogen, preferably chloro, in the presence of an alkaline earth metal oxide, preferably in the presence of magnesium oxide, under pressure, preferably at 1.1 to 4 bar, with a compound of formula (6), wherein Y is $C_2$–$C_4$alkanoyl or sulfomethyl, preferably acetyl, and carrying out the saponification in acid aqueous medium. The preferred temperatures for these reactions are those given above. It is very particularly preferred to carry out the reaction of the compound of formula (5) with the compound of formula (6) in an inert gas atmosphere, preferably under nitrogen.

The compounds of formulae (2) and (3) are known or can be prepared in analogy to known compounds.

If the compounds of formula (2) contain a sulfo group, they are obtained either in the form of their free acid or, preferably, as the salts thereof.

Suitable salts are typically the alkali metal salts or ammonium salts, or the salts of an organic amine.

Typical examples are the sodium, lithium, potassium or ammonium salts, or the salt of the mono-, di- or triethanolamine.

The compounds of formula (1) obtainable according to the novel process are suitable e.g. for the preparation of dyes. The compounds of formula (1) prepared according to this invention can typically be used as intermediates, e.g. as diazo components, for the preparation of azo dyes. The dyes obtainable with the compounds of formula (1) prepared according to this invention are suitable for dyeing nitrogen-containing or hydroxyl group-containing fibre materials. The dyes are prepared according to per se known methods, typically using known diazotisation and coupling reactions.

The compounds of formula (1) in the novel process are obtained in good yield and purity.

The dyes obtainable with the compounds of formula (1) prepared according to this invention give level dyeings of good allround fastness properties, in particular good fastness to rubbing, wet treatment, wet rubbing and light. These dyes also dye in a brilliant shade.

In the following Examples, parts are by weight. The relationship between parts by weight and parts by volume is the same as that between the gram and the cubic centimeter.

EXAMPLE 1

A pressure autoclave is charged in succession with 10.2 parts of water, 3.8 parts of 4-chloro-3-nitrobenzene-1-sulfonic acid, 2.65 parts of 4-aminoacetanilide and 0.89 part of magnesium oxide. The autoclave is closed at room temperature, flushed with nitrogen and then heated, with stirring, to a temperature of 120° C. in the vessel. The pressure is c. 2 bar. The batch is stirred for c. 24 hours under these reaction conditions and then cooled to 90° C. The pressure in the autoclave is released, the batch is diluted with c. 34 parts of water, the temperature is adjusted to 90° C. and 14 parts of hydrochloric acid (32%) are added dropwise over 20 minutes. After 4 hours under reflux, the saponification is complete. The reaction mixture is cooled to 60° C. and the product is collected by suction filtration. The product is washed with a mixture of water and 32% hydrochloric acid (at a ratio of 4:1), to give the compound of formula

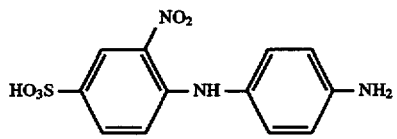

(101)

in good yield and purity.

Dye Synthesis:

A solution of 40 parts of the compound of formula (101), obtainable according to Example 1, in 500 parts of water and 12 parts of a 36% solution of sodium hydroxide is stirred at 20° C., and 60 parts of a 2N solution of sodium nitrite are added. This mixture is added, with stirring, over 20 minutes and in the temperature range from 10° to 15° C. to 30 parts of hydrochloric acid (36%) in 400 parts of water. After stirring for 1 hour at a temperature of 10° to 15° C., the diazo suspension is added over 30 minutes at 0° to 5° C. to a stirred solution of 11 parts of o-chlorophenol in 500 parts of water, 20 parts of a 36% solution of sodium hydroxide and 20 parts of sodium carbonate. Stirring is continued for a further 16 hours and the product is then isolated by filtration, washed and dried, to give the dye of formula

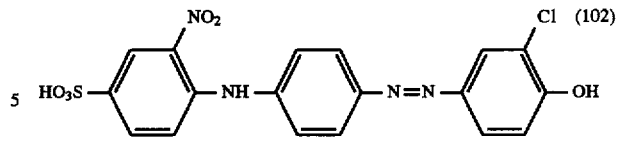

(102)

which dyes in a brilliant shade.

An analogous dye is obtained by repeating the above dye synthesis, but replacing 11 parts of o-chlorophenol with an equimolar mount of m-cresol.

What is claimed is:

1. A process for the preparation of a compound of formula

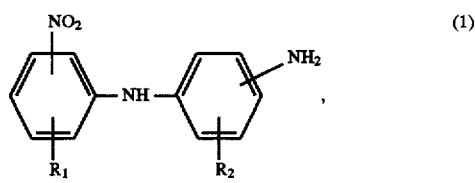

(1)

in an aqueous medium, wherein $R_1$ is hydrogen, $C_1$–$C_4$-alkyl or sulfo, and $R_2$ is hydrogen or $C_1$–$C_4$alkyl, which process comprises reacting a compound of formula

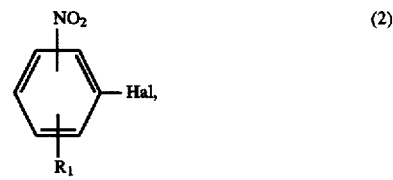

(2)

wherein Hal is halogen and $R_1$ has the meaning given above, with a compound of formula

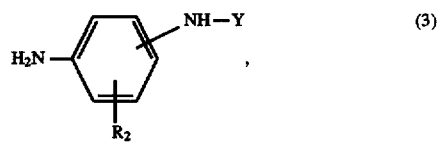

(3)

in the presence of an alkali metal hydroxide, an alkali metal carbonate or an alkaline earth metal oxide, wherein Y is a saponifiable group and $R_2$ has the meaning given above, to give the compound of formula

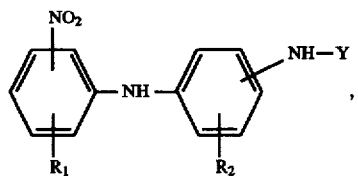

(4)

wherein $R_1$, $R_2$ and Y have the meanings given above, and saponifying the compound of formula (4) to give the compound of formula (1).

2. A process according to claim 1, wherein $R_1$ is sulfo.

3. A process according to claim 1, wherein $R_2$ is hydrogen.

4. A process according to claim 1, wherein the compound of formula (2) is a compound of formula

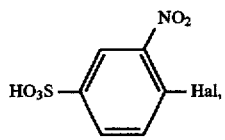

wherein Hal is halogen, and the compound of formula (3) is a compound of formula

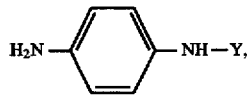

wherein Y is a saponifiable group.

5. A process according to claim 1, wherein Hal is chloro.

6. A process according to claim 1, wherein Y is $C_2$–$C_4$alkanoyl or sulfomethyl.

7. A process according to claim 1, wherein the reaction of the compound of formula (2) with the compound of formula (3) is carried out under pressure.

8. A process according to claim 1, wherein the saponification of the compound of formula (4) is carried out in acid aqueous medium.

9. A process according to claim 4, which comprises reacting a compound of formula (5), wherein Hal is halogen, in the presence of an alkaline earth metal oxide, under pressure, with a compound of formula (6), wherein Y is $C_2$–$C_4$alkanoyl or sulfomethyl, and carrying out the saponification in acid aqueous medium.

10. A process according to claim 1, wherein the reaction of the compound of formula (2) with the compound of formula (3) is carried out in an inert gas atmosphere.

11. A process according to claim 1, wherein the reaction of the compound of formula (2) with the compound of formula (3) is carried out in the temperature range from 80° to 150° C.

12. A process according to claim 1, wherein the saponification is carried out in the temperature range from 80° to 120° C.

* * * * *